US009234902B2

(12) United States Patent (10) Patent No.: US 9,234,902 B2
Önundarson et al. (45) Date of Patent: Jan. 12, 2016

(54) METHOD FOR MONITORING ANTICOAGULANT THERAPY

(76) Inventors: Pall Torfi Önundarson, Reykjavik (IS); Brynja R. Gudmundsdottir, Reykjavik (IS)

( * ) Notice: Subject to any disclaimer, the term of this patent is extended or adjusted under 35 U.S.C. 154(b) by 0 days.

(21) Appl. No.: 13/414,112

(22) Filed: Mar. 7, 2012

(65) Prior Publication Data

US 2012/0231485 A1 Sep. 13, 2012

(30) Foreign Application Priority Data

Mar. 8, 2011 (IS) .......................... 050010

(51) Int. Cl.
*G01N 33/86* (2006.01)
*C12Q 1/56* (2006.01)

(52) U.S. Cl.
CPC . *G01N 33/86* (2013.01); *C12Q 1/56* (2013.01)

(58) Field of Classification Search
None
See application file for complete search history.

(56) References Cited

U.S. PATENT DOCUMENTS

| 3,179,567 | A | * | 4/1965 | Owren ............................ 435/13 |
| 3,395,210 | A | * | 7/1968 | Phillips et al. .................. 435/13 |
| 4,160,025 | A | * | 7/1979 | Eibl et al. ..................... 514/14.3 |
| 4,784,944 | A |   | 11/1988 | Kolde |
| 5,447,440 | A | * | 9/1995 | Davis et al. .................. 435/6.16 |
| 2001/0004641 | A1 |   | 6/2001 | Hawkins |
| 2010/0086953 | A1 |   | 4/2010 | Kappel et al. |

FOREIGN PATENT DOCUMENTS

WO 9307491 A1 4/1993
WO 2004102202 A1 11/2004

OTHER PUBLICATIONS

Chan E et al. (1987). Inter-relationshop among individual vitamin K-dependent clotting factors at different levels of anticoagulation. Br. J. Clin. Pharmac., v24, p. 621-625.*
Cate-Hoek AJ and Prins MH (2004). Appropriate level and length of postthrombic warfarin treatment: an evaluation of recent developments. Curr. Opin. Hematol., v11, p. 182-186.*
Zivelin A et al. (1993). Mechanism of the Anticoagulant Effect of Warfarin as Evaluated in Rabbits by Selective Depression of individual procoagulant vitamin K-dependent clotting factors. Journal of Clinical Investigation, v92, p. 2131-2140.*
Lind SE et al. (1997). Plasma levels of factors II VII and X and their relationship to the international normalized ratio during chronic Warfarin therapy. Blood Coagulation and Fibrinolysis, v8, p. 48-53.*
Zivelin et al. (1993). Mechanism of the Anticoagulant Effect of Warfarin as Evaluated in Rabbits by Selective Depression of Individual Procoagulant Vitamin K-dependent Clotting Factors. J. Clin. Invest., v92, p. 2131-2140.*

Middleton et al. (1973). A Therapeutic Concentrate of Coagulation Factors II, IX and X from Citrated, Factor VIII-Depleted Plasma. Vox Sanguinis, v24(5), p. 441-456.*
Robson et al. (2009). Familial multiple coagulation factor deficiencies—chance associations and distinct clinical disorders. Haemophilia, v15, p. 11-19.*
van Geest-Daalderop et al. (2005). Preanalytical Variables and Off-Site Blood Collection: Influences on the Results of the Prothrombin Time/International Normalized Ratio Test and Implications for Monitoring of Oral Anticoagulant Therapy. Clinical Chemistry v51(3), p. 561-568.*
Kuruvilla et al. (2001). A review of warfarin dosing and monitoring. BUMC Proceedings, v14, p. 305-306.*
Horsti (2009). A sensitivity comparison of the Quick and Owren prothrombin time methods in oral anticoagulant therapy. Hematology Reviews 2009; vol. 1(e15), p. 87-91.*
Nielsen et al (2005). Effects of coagulation factor deficiency on plasma coagulation kinetics determined via thrombelastography® : critical roles of fibrinogen and.factors II, VII, X and XII. Acta Anaesthesiol Scand, v49, p. 222-231.*
von dem Borne et al. (1996). Effect of Heparin on the Activation of Factor XI by Fibrin-bound Thrombin.Thrombosis and Haemostasis, v76(2), p. 347-353.*
Brummel et al., "Oral Anticoagulation Thresholds", Circulation 104, 2001, pp. 2311-2317.
Costa et al., "Usefulness of factor II and factor X as therapeutic markers in patients under chronic warfarin therapy", Biomedicine & Pharmacotherapy 64, 2010, pp. 130-132.
Favaloro et al., "Improving the harmonisation of the International Normalized Ration (INR): time to think outside the box?", Clin. Chem. Lab Med., 48(8), 2010, pp. 1079-1090.
Furie et al., "Comparison of the native prothrombin antigen and the prothrombin time for monitoring oral anticoagulant therapy", Blood 64, 1984, pp. 445-451.
Furie et al., "Randomized Prospective Trial Comparing the Native Prothrombin Antigen with the Prothrombin Time for Monitoring Oral Anticoagulant Therapy", Blood, vol. 75, No. 2, 1990, pp. 344-349.
Hirsh, MD., "Optimal Intensity and Monitoring Warfarin", The American Journal of Cardiology, vol. 75, 1995, pp. 39B-42B.

(Continued)

*Primary Examiner* — Scott Long
*Assistant Examiner* — Sean C Barron
(74) *Attorney, Agent, or Firm* — Cantor Colburn LLP (57) ABSTRACT

A method of measuring the combined activity of both and only coagulation factors II and X for the purpose of monitoring anticoagulant therapy, and kits for using the method. The method involves mixing of test plasma from a human to be tested with specially prepared plasma deficient in both and only coagulation factors II and X but with normal levels of other factors (referred to herein as Fiix-deficient plasma or Fiix plasma), in order to correct for any possible deficiency in other coagulation factors than FII and FX in the test sample. By adding a coagulation reagent and calcium, the generation of thrombin or fibrin can be measured. Kits of the invention comprise a coagulation reagent, calcium and specially made plasma that is deficient in both and only factor II and factor FX.

16 Claims, 7 Drawing Sheets

(56) References Cited

OTHER PUBLICATIONS

Kornberg et al., "Comparison of Native Prothrombin Antigen with the Prothrombin Time for Monitoring Oral Anticoagulant Prophyaxis", Circulation, vol. 88, No. 2, 1993, pp. 454-460.

Owren et al., "The Control of Dicumarol Therapy and the Quantitative Determination of Prothrombin and Proconvertin", Dept. of Internal Medicin. Unv. of Oslo, 1951, pp. 201-208.

Quick et al., "A Study of the Coagulation Defect in Hemophilia and in Jaundice", J. Bio. Chem. 190, 1935, pp. 501-511.

Rosborough et al., "Factor X and factor II activty levels do not always agree in warfarin-treated lupus anticoagulant patients", Blood Coagulation and Fibrinolysis, 21; 2010, pp. 242-244.

World Health Organization; "Guidelines for Thromboplastins and Plasma Used to Control Anticoagulant Therapy", WHO Technical Report Series, No. 889, 1999, pp. 64-93.

Xi et al., "The Releative Importance of the Factors II, VII, IX and X for the Prothrombinase Activity in Plasma of Orally Anticoagulated Patients", Thrombosis and Haemostasis, 62(2), 1989, pp. 788-791.

Zivelin et al., "Mechanism of the Anticoagulant Effect of Warfarin as Evaluated in Rabbits by Selective Depression of Individual Procoagulant Vitamin K-depressant Clotting Factors", J. Clin. Invest., vol. 92, 1993, pp. 2131-2140.

Roberts et al., "CH 31: Other Coagulation Factor Deficiencies", Thrombosis and Hemorrage, 3rd ed, S.A.I. Loscalzo. J. vol. 1, 2003, pp. 579-598.

Gudmundsdottir et al.; "Critical Role of Factors II and X During Coumarin Anticoagulation and Their Combined Measurement with a New Fiix-prothrombin Time"; Thrombosis Research; 130; pp. 674-681; (2012).

Onundarson PT et al.; "Warfarin Monitoring with the Fiix-prothrombin Time (Fiix-INR) Increases Time Within Target Range and Reduces Dose Adjustment Need Compared to Standard Monitoring Using INR"; Journal of Thrombosis and Haemostasis; Suppl 2; pp. 290-1019; Abstract of p. 467 only; (2013).

International Search Report; International Application No. PCT/IS2012/050005; International Filing Date Mar. 8, 2012; Date of Mailing Oct. 15, 2012; Applicant's File Reference ANF0017US; 5 pages.

Wallentin et al.; "Efficacy and Safety of Dabigatran Compared with Warfarin at Different Levels of International Normalised Ratio Control for Stroke Prevention in Atrial Fibrillation: An Analysis of the RE-LY Trial"; Lancet; 376; pp. 975-983; (2010).

Lippi & Favaloro; "Laboratory Monitoring of Warfarin in the Era of Direct Oral Anticoagulants"; The Lancet Haematology; online http://dx.doi.org/10.1016/S2352-3026(15)00075-7; May 26, 2015.

Onundarson et al.; "Fiix-prothrombin Time Versus Standard Prothrombin Time for Monitoring of Warfarin Anticoagulation: A Single Centre, Double-blind, Randomised, Non-inferiority Trial"; The Lancet Haematology ; online http://dx.doi.org/10.1016/S2352-3026(15)00073-3 May 26, 2015.

\* cited by examiner

METHOD FOR MONITORING ANTICOAGULANT THERAPY

CROSS REFERENCE TO RELATED APPLICATIONS

This application claims priority to Icelandic Application No. IS 050010, filed on 08 Mar. 2011, the disclosure of which is also incorporated herein by reference.

FIELD OF INVENTION

The present invention is within the field of medical diagnosis and drug monitoring, specifically the field of measuring of blood coagulation in patients taking pharmaceutical compounds for anticoagulation therapy.

TECHNICAL BACKGROUND AND PRIOR ART

Blood clotting is the mechanism that prevents continuing blood loss when any part of the blood circulation system is injured. It involves the formation of a semi-solid mass of blood material, which acts to plug vessel wounds. The system comprises series of interacting components in the blood and in the vessel wall that must remain in balance; an inactive system causes risk of severe and fatal bleeding, whereas excessive activity of the blood clotting system causes risk of blood clot formation (thrombosis and thromboembolism) within the circulatory system, clogging arteries, with potentially fatal consequences due to tissue necrosis (cell death).

Anticoagulants or "blood thinners" are among the most frequently administered drug classes and within this class, vitamin K antagonists (VKA, coumarins) have until lately been the only available oral agents. Due to the delicate balance of the blood clotting system and much variation in patient sensitivity and responsiveness to the therapy, VKA doses have to be carefully adjusted and continuously monitored, as patient response and suitable dose frequently changes with time. An estimated 800 million tests are performed annually worldwide to monitor the blood clotting in patients on VKA.

The blood coagulation system comprises a complex system of inter-linked proenzymes, enzymes and cofactors, performing their role on the surface of activated platelets and endothelial cells and in ruptured vessels in the human body. When the system is activated, usually in a vessel wound, the ultimate result is the formation of a blood clot containing an insoluble fibrin mesh. In the body, the coagulation process is carefully controlled on the surface of activated platelets and endothelial cells, but in the testing laboratory, the platelet surface is usually substituted with suitable phospholipids. The proenzymes, enzymes and cofactors are traditionally named coagulation factors (F), most of whom are formed in the liver.

Vitamin K dependent coagulation factors and vitamin K antagonists: Four coagulation factors, ie FII, FVII, FIX and FX, that are formed in the liver, are inactive unless following synthesis they become further carboxylated by a vitamin K dependent enzyme process in the liver. In patients deficient in vitamin K or in patients treated with a vitamin K antagonist (VKA), the amount of carboxylated vitamin K dependent (VKD) factors is reduced and, hence, also the clottability (coagulability) of the relevant patient's blood. Unless the effect of VKA is controlled this may lead to severe and even fatal internal hemorrhage. But by reducing the VKD factor levels in a controlled manner, abnormal blood clotting within the vessels (thrombosis) can be prevented while minimizing the risk of bleeding. It is therefore imperative that the effect of VKA be monitored with appropriate coagulation tests. Based on test results, the dose can then be adjusted maximizing the antithrombotic effect and at the same time minimizing the risk of abnormal bleeding caused by over-anticoagulation.

The monitoring of blood clotting activity in VKA patients has for over sixty years been based on measuring the prothrombin time (PT), either as the original Quick PT (PT) (Quick, A., *J Bio Chem* 1935(109): p. 73-4) or as it's modification, the Owren's PT (also known as PP, P&P-test or prothrombin complex test)(Owren and Aas. *Scand J Clin Lab Invest*, 1951. 3(3): p. 201-8.). The PT test measures the clotting activity of three out of four vitamin K dependent clotting factors (i.e. FII, FVII, and FX) as well as that of fibrinogen (factor I) and factor V, in a blood plasma sample which has been depleted from calcium, by adding a coagulation reagent (thromboplastin, tissue factor) and calcium, and subsequently measuring the time that it takes the blood to coagulate. The latter test (P&P) is a modification of the PT, where adsorbed plasma (totally deficient in vitamin K dependent factors) is mixed into the test plasma, correcting for any possible deficiency of factor V or fibrinogen and leaving the P&P test only sensitive to factors II, VII and X. Hence, the PT test is also sensitive to deficiency of factors V and fibrinogen, which are not vitamin K dependent and if deficient may confound results in patients taking VKA. With both tests, however, the measured clotting time is equally sensitive to a reduction in any of the three vitamin K dependent factors that the test measures, i.e. FII, FVII and FX. FIX coagulant activity is not measured by these tests. The clotting times obtained with the PT based tests have in practice been presumed to directly reflect the antithrombotic effect of VKA in patients except during initiation of VKA therapy. However, this may not always be the case.

The actual measured clotting time measured on a normal individual will vary, depending on the method applied and also the analytical system and specific reagents used. Different coagulation reagents and even different batches of manufacturers' tissue factor (thromboplastin) and proteins used cause variability in the clotting time obtained with the PT or P&P. Therefore, a protocol for calibrating methods has been devised. Each manufacturer assigns an ISI value (International Sensitivity Index) for the provided tissue factor. (See *WHO Guidelines for Thromboplastins and Plasma Used to Control Anticoagulant Therapy*, TRS, No 889, Annex 3.) The ISI value indicates how a particular batch of tissue factor compares to an internationally standardized sample. The ISI is usually between 1.0 and 2.0. An "International normalised ratio" value (INR) can thus be calculated, which is the ratio of a patient's prothrombin time to the mean normal population PT, raised to the power of the ISI value for the analytical system used. The INR value can accordingly be described with the equation:

$$INR = (PT/MNPT)^{ISI}$$

where MNPT refers to "mean normal prothrombin time". For practical purposes the MNPT is generally obtained as a mean value of prothrombin times of at least 20 fresh samples from healthy individuals. A high INR level, such as INR over 5, indicates that there is a high chance of bleeding, whereas if the INR is 1.3 or less, there is no protection against having thromboembolism. A normal INR range for a healthy person is 0.8-1.3 and for people on coumarin therapy (e.g. warfarin), the most commonly recommended therapeutic range is 2.0-3.0. The target INR may be set higher in particular situations, such as for individuals with mechanical heart valves.

Modified tests for accurately assessing blood clottability that could overcome disadvantages of present methods in the art, and make possible more accurate dose adjustment and preferably less frequent monitoring of the anticoagulant activity in anticoagulated patients, would be greatly appreciated.

SUMMARY OF INVENTION

The present invention relates to a new method of monitoring anticoagulant therapy and kits for using the method. This is based on inventors' experiments indicating that measurement of only the activity of factors II and X (FII and FX) more accurately reflects clottability than present conventional methods (PT, P&P) and, hence, likely the antithrombotic effect of VKA anticoagulants in patients is better indicated by the new test method. The invention is based on determining the combined activity of only coagulation factors II and X and excluding the influence of all other coagulation factors on the test results. The method involves mixing of test plasma from a human to be tested with plasma deficient in both and only coagulation factors II and X but with normal levels of other factors (herein referred to as Fiix-deficient plasma), in order to correct for any possible deficiency in other coagulation factors than FII and FX in the test sample, that might otherwise influence the test result. By adding a coagulation reagent and calcium, the generation of thrombin or fibrin can be measured. In this manner the activity of factors II and X and their combined activity can be accurately assessed without a confounding effect of other factor deficiencies. Thus, the invention provides an assessment of blood clottability, which the inventors believe that more accurately than current methods reflects the antithrombotic effect of VKA anticoagulant agents administered to the subject being tested.

The invention further provides kits that are suitable for performing the method of the invention, which comprise a coagulation reagent and plasma deficient in both and only factors II and X.

BRIEF DESCRIPTION OF FIGURES

FIG. 1: Quick prothrombin time (PT, panel A) or Owren's prothrombin time (P&P, panel B) in relation to selective reduction in individual vitamin K dependent factor activity.

DETAILED DESCRIPTION

The present invention involves a novel method and provides kits based on the method, for determining blood clottability of human plasma samples, in particular for measuring the activity of an anticoagulant drug in patients taking such drugs. The influence of other coagulation factors than FII and FX is eliminated by this method. The method may improve in particular anticoagulant therapy with coumarins (vitamin K antagonists, VKA) such as warfarin, which reduce the concentration of active (gamma-carboxylated) coagulation factors II, VII, IX and X. The new method may also have application in order to monitor other anticoagulants that inhibit FII or FX or both.

The underlying foundation of our invention is based on experimental results which suggest that including the influence of coagulation FVII on the clotting time in patients on VKA, as is done in conventional prothrombin time based assays, PT (Quick) and P&P (Owren), for determining blood clottability, may cause a fluctuation in the determined clotting time results that may be therapeutically irrelevant. Such confounding test results may possibly mislead the clinician when adjusting the dose of these potentially dangerous medications. This new hypothesis has led to a new invention, which is based on the following considerations and experimental results:

I. During initiation of oral anticoagulation (OA) with VKA and following dose changes, the concentration of each of the physiologically active gamma carboxylated vitamin K dependent (VKD) coagulation factors (F) is affected to a different degree and at a different rate due to their significantly different half-lifes, i.e. about 3.5 hours for FVII (proconvertin), 52 hours for FX (Stuart factor) and 72 hours for FII (prothrombin) (Roberts, H. R., Escobar M. A., *Other coagulation factor deficiencies*. 3rd ed. Thrombosis and Hemorrhage, ed. S.A.I. Loscalzo J. Vol. 1. 2003, Philadelphia: Lippincott Williams & ns. 575-598). Accordingly, FVII concentration changes faster than the other factors and this may have a major influence on measured PT/P&P values, even when FII and FX have not changed significantly.

II. Some prior studies have indicated that the antithrombotic influence of FVII during coumarin therapy may be less important than that of prothrombin (FII) or FX (Zivelin et al, *J Clin Invest*, 1993. 92(5): p. 2131-40; Xi et al, *Thromb Haemost*, 1989. 62(2): p. 788-91). Xi et al showed that prothrombinase activity (thrombin generation) in anticoagulated samples from patients on coumarins was dependent on the FX and in particular FII concentration but less dependent on the activity of FVII, which demonstrated a threshold relationship first evident at very low FVII concentrations. Zivelin et al. found that the antithrombotic effect of VKD factors in rabbits depend on the concentration of FX and in particular on the FII concentration but not on the concentration of FVII. Further, it was shown in clinical studies, that monitoring VKA by measuring the native prothrombin antigen (NPA) by ELISA appeared to be more predictive of adverse events than monitoring with the PT, suggesting a certain inaccuracy of PT measurements (Furie et al, *Blood*, 1984. 64(2): p. 445-51; Furie et al, *Blood*, 1990. 75(2): p. 344-9; Kornberg et al, *Circulation*, 1993. 88(2): p. 454-60). Finally, the study of Brummel et al. using anticoagulated plasma from patients on warfarin demonstrated that a poor relationship existed between the PT based clotting times (INR) and thrombin generation in response to dilute tissue factor (Brummel et al, *Circulation*, 2001. 104(19): p. 2311-7). Our findings using rotational thromboelastometry (ROTEM) and dilute tissue factor confirm this observation, indicating inaccuracy of the PT or P&P based monitoring methods.

The term "test plasma" or "test plasma sample" refers in this context to plasma from a patient or subject for whom a blood clotting test is desired.

"Normal plasma" refers to plasma suitable for use as control, from normal healthy individuals, preferably and typically pooled from several individuals to normalise any inter-individual variation in concentration of relevant factors.

"Coagulation reagent" refers to a reagent that triggers the coagulation pathway in a blood or plasma sample, that leads to the conversion of prothrombin to thrombin and fibrinogen to fibrin.

The method of the invention is based on measuring combined activity of both and only coagulation factors II and X, meaning that the effect from other factors that may be variable in the test sample (e.g. FI, FV, FVII and FIX) is eliminated. "Combined activity" herein refers to measured effects due to activity of both FII and FX, but the effect of one is not differentiated from the other.

In the method of the invention, the test plasma sample is mixed with Fiix-deficient plasma, as mentioned above, the ratio of the test plasma to the deficient plasma is suitably in the range from 1:1 to 1:20, preferably in the range 1:4 to 1:10, such as in the range from 1:5 to 1:8, such as but not limited to 1:5, 1:6, 1:7, 1:8, or 1:10. As used herein the notation 1:4 means one part test plasma against four parts deficient plasma, i.e. five parts plasma in total (i.e. 20% test plasma and 80% deficient plasma).

Generally, the plasma test sample is treated as for conventional coagulation tests, i.e. a fresh blood sample drawn from the patient is treated with citrate for calcium depletion, and red blood cells are separated from the plasma by centrifugation. The prepared test plasma sample can then conveniently be mixed with Fiix deficient plasma, suitably just prior to analysis.

A coagulation reagent is added to the test plasma, and calcium, to trigger coagulation. The coagulation reagent and calcium can be pre-mixed together or each added separately to the test plasma sample. Alternatively, either or both reagents can be pre-mixed with the deficient plasma. Accordingly, the steps of the claimed method involving mixing of test plasma sample with deficient plasma and adding the coagulation reagent and calcium can be performed in one, two or three steps.

The coagulation reagent can be any of the commonly used reagents in conventional tests as those described above, such as but not limited to thromboplastin (including recombinant tissue factor), phospholipids, factor IXa, factor XIa, factor XIIa, kallikrein, factor VIIa, factor VIIa and exogenous activator such as snake venom that activates factor X.

The present method works both with activation of coagulation through the intrinsic pathway or extrinsic pathway. The coagulation reagents thromboplastin and factor VIIa will activate the extrinsic pathway, whereas the following coagulation reagents activate the intrinsic pathway: phospholipids, factor IXa, factor XIa, factor XIIa, kallikrein, or factor IXa/VIIIa complex.

Exogenous activators such as snake venoms can be used in the method of the invention. These include Russel's viper venom (snake venom from *Daboi russelii*) which can obtained from natural source or recombinantly produced. Other snake venoms which activate factor X directly, through the common pathway may also be used.

Thromboplastin is not a pure protein, but a complex of tissue factor protein and phospholipids. Tissue factor (also referred to as platelet tissue factor, factor III, thrombokinase or CD142) is an integral transmembrane protein which is a cell surface receptor for factor VIIa, functioning as a cofactor mandatory for the proteolytic activity of factor VIIa towards factor X converting factor X to the active protease factor Xa. Tissue factor needs to be associated with coagulant phospholipids for the full expression of its cofactor function.

Thromboplastin used in the method and kits of the invention can be obtained from animal sources as are known to the skilled person, including but not limited to rabbit brain, human placenta, human brain, bovine brain, bovine lung, or other suitable sources. Thromboplastin can as well be recombinantly produced thromboplastin which is preferably recombinant human thromboplastin. Recombinant thromboplastin can be produced by expressing the tissue factor component in suitable cell culture, e.g. placental mouse cell culture, hamster ovary cells (CHO cells); fungal cells, prokaryotic organisms, e.g. in *E. coli* cultures; transgenic plants or other suitable expression vehicle, and subsequently the tissue factor is lipidated in vitro.

In some embodiments of the invention, the coagulation reagent comprises phospholipids, these may be derived form various natural sources or synthesized and/or modified chemically. Phospholipids used in coagulation tests are also referred to as partial thromboplastin, though typically partial thromboplastin refers to phospholipids extracts separated from various tissues. When using phospholipids as coagulation reagent, these can preferably be of suitable composition, enriched in phospholipids that have good procoagulant activity, such as but not limited to phosphatidyl serine. The coagulation reagent may in certain embodiments be used with an activator, in particular, when phospholipids are used as coagulation reagent. Such activator can be suitably selected from but is not limited to kaolin particles, celite, glass particles, silica particles, which may or may not be micronized silica, or ellagic acid. In this embodiment, the method corresponds to what is referred to as the APTT test (activated partial thromboplastin time) except that according to the invention, Fiix-deficient plasma is added, making the Fiix-APTT test results only reflect the activity of FII and/or FX. When using phospholipids without activator as the test reagent, the test can be compared to what is referred to as the PTT test, i.e. Fiix-PTT.

Combinations of more than one coagulation reagent are used in certain embodiments, such combinations include using thromboplastin and factor VIIa, and a combination of factor IXa and VIIIa.

The calcium source is generally but not necessarily calcium chloride.

The amount/concentration of coagulation reagent in the method is generally similar as in current methods for measuring coagulation. When thromboplastin is used, the results can be normalized based on ISI value, suitably done as in normalization of Quick PT and the Owren PT tests.

The coagulation reagent and/or deficient plasma are preferably lyophilised and in such case are reconstituted prior to use in water or suitable buffer.

Calcium is used in conventional concentration, such as in the range 1.0-4.0 mM, preferably 2.5 mM.

Endpoint Determination:

The endpoint determination in the method of the invention can be of any conventional presently used type, including but not limited to manual (visual) determination by tilt-tube technique, mechanical detection using methods of clot detection such as "rolling ball" or vibrating probe technique (detecting when probe is static due to higher viscosity), optical detection methods using optical detection of fibrin formation, and also chromogenic techniques based on the use of chromogenic substrates, including substrates for thrombin (e.g. substrate S2238 (Chromogenix-Instrumentation Laboratory SpA, Milano, Italy) and substrates for FXa, such as BIOPHEN CS-11 (22) (Aniara, Mason Ohio, USA).

Other embodiments include the use of fluorogenic substrates, that upon cleavage by an amidolytic enzyme (e.g. thrombin, or factor Xa) release a fluorogenic marker. These include but are not limited to peptide-4-methylcoumarin amides (MCA), e.g. Pefafluor Fxa (Pefa-5534) (Pentapharm Ltd. Basel, Switzerland) which is a sensitive substrate for factor Xa. In other embodiments, luminogenic substrates are used, these include the substrate S-2613 (t-butyloxycarbonyl-isoleucyl-glutamyl-gamma-piperidyl-glycyl-arginyl-isoluminol), for other substrates, see e.g. Hemker H. C., *Handbook of synthetic substrates for the coagulation and fibrinolytic system*, Martinus Nijhoff Publishers, Boston (1983).

Kits of the Invention:

In another aspect, the invention provides kits which are suitable for operating the method of the invention in clinical laboratories around the world. Accordingly, the kits are configured to provide in suitable amount and ready-to-use containers the necessary reagents for running tests according to the invention. The test kit of the invention comprises a coagulation reagent such as one or more of the above mentioned in the description of the methods of the invention, and normal plasma that is deficient in only factor II and factor X (Fiix-deficient plasma).

The deficient plasma is plasma that is deficient only in factor II and factor X, such that it still contains other coagulation factors including factor VII and IX. The deficient plasma is suitably produced as described above, i.e. normal plasma as defined above that is made deficient in FII and FX, preferably with immunodepletion methods.

In some embodiments, the kits of the invention further comprise a calcium ion source, which can be provided in its own designated container or included with the coagulation reagent or the deficient plasma. In other embodiments, calcium is not provided as part of the kit, as many laboratories and coagulation apparatuses have suitable sources of calcium reagent.

The coagulation reagent and said deficient plasma can in certain embodiments be provided in one single container which can further be provided with or without calcium ions. In other embodiments the coagulation reagent and deficient plasma are provided in separate containers.

The coagulation reagent and deficient plasma are preferably provided in lyophilised powder form, whether or not these are provided separate or combined in the same vial. The one or more containers are suitably configured such that the lyophilised material can be reconstituted in the original container.

EXAMPLES

Experimental Part

We were interested in studying the contribution of each VKD coagulation factor on coagulation as measured by rotational thromboelastometry (ROTEM). The results of these experiments led us to believe that the influence of FII and FX carried substantially more weight on clot formation than FVII and FIX at clinically relevant concentrations of these factors. However, we could not discern a difference between the effect of FII and FX. This observation led to our new invention as described below.

We are not aware of a prior study using ROTEM activated with highly diluted thromboplastin to systematically evaluate the contribution of each of the vitamin K dependent coagulation factors on clot formation. ROTEM is a global coagulation assay usually done on whole blood. The ROTEM method, in addition to measuring the time to initiation of fibrin polymerization, i.e. clotting time (ROTEM CT, initiation phase) also measures the consequent aspects of coagulation (Rand et al, *Blood,* 1996. 88(9): p. 3432-45), including the rate of the subsequent propagation phase of bulk clot formation (measured as alpha angle or ROTEM maximum velocity, "MaxVel") and finally the maximum clot firmness (MCF), which reflects the final stabilization phase (Sorensen et al, *J Thromb Haemost,* 2003. 1(3): p. 551-8). ROTEM results done on whole blood are a function not only of coagulation factors but also of platelet function, proteases, inhibitors and the fibrinolytic system. ROTEM, in the view of some investigators, better describes clot formation than traditional coagulation assays done on PPP since traditional coagulation tests only measure the initiation phase (Ganter et al, *J Cardiothorac Vasc Anesth,* 2008. 22(5): p. 675-80). Since we were unable to do the experiments on whole blood we compared experiments done on PPP with experiments with added platelet phospholipid or blood bank platelets. For the most part the results were similar, unless otherwise stated. In our ROTEM experiments we used a highly diluted thromboplastin (1:17,000) which may more closely reflect the physiological concentration of tissue factor than the high thromboplastin concentration used in the PT assays (Brummel et al, above).

Experimental Reagents and Conditions:

Plasma and Platelet Preparation

Blood was drawn from patients on warfarin anticoagulation for making PPP test samples. Blood was also drawn from twenty healthy donors (10 men, 10 women) for making pooled normal plasma (PNP), for coagulation testing and ROTEM analysis. Using a minimal stasis technique, blood was drawn through a 21 G needle into 1/10 vol/vol 3.2% (0.109 mol/L) buffered sodium citrate Vacuette@ tubes (Greiner, Kremsmunster, Austria). Platelet poor plasma (PPP) was prepared by centrifugation of the blood at 4° C. for 15 minutes at 2,500 g, removal of supernatant and recentrifugation for 15 minutes at 2,500 g. The PNP was prepared by combining the recentrifuged normal plasma and the final material was stored in 0.5 mL aliquots at −80° C. Immunodepleted factor deficient plasmas were obtained from Haematologic Technologoies Inc. (Essex Junction, Vt., USA). The immunodepleted plasmas were selectively depleted of coagulation factors II, VII, IX or X and there was no residual inhibitory activity in the plasmas.

Frozen-thawed (burst) platelets (platelet phospholipid) and washed platelets were made from freshly donated blood bank platelet concentrate in acid-citrate dextrose (ACD). For both, platelets were washed in the following manner: The platelet-rich plasma (PRP) was centrifuged for 15 minutes at 2,500 g and ten resuspended 1:1 vol/vol in TBS buffer (6.055 g Trizma base (Sigma, Seetze, Germany), 8.766 g NaCL, pH 7.4, 1000 mL $H_2O$). After resuspension the tubes were filled with TBS buffer and re-centrifuged for 10 min at 2,500 g. The supernatant was removed and the pellet was resuspended twice. The final suspension was counted automatically using Sysmex 4000 (Sysmex Corp., Kobe, Japan) and the final solution adjusted to a platelet count of $100 \times 10^9$/L. The final solution was either frozen at −80° C., thawed again and then re-aliquoted in small tubes and frozen again to make platelet phospholipids, or alternatively, washed platelets were stored at room temperature and used within two days.

Reagents

Factor deficient plasmas used for assaying coagulation factors were obtained from Diagnostica Stago (Asnieres, France). Hepes buffer (Hepes 20 mM, NaCl 150 mM, with and without $CaCl_2$ 200 mM, pH 7.4) was obtained from Bie and Berntsen Inc. (Herlev, Denmark). Recombinant thromboplastin (TF) (Innovin®) was obtained from Dade Behring (Marburg, Germany). The Innovin was reconstituted and stored in 100 μL aliquots at 80° C. in Eppendorf tubes. One tube of Innovin was reconstituted for each experiment and 10 μL Innovin were mixed into 990 μL of Hepes $CaCL_2$ to make a 1:100 dilution which was further diluted by mixing 100 μL of the 1:100 dilution with 500 μL of Hepes $CaCL_2$ to make a 1:600 working solution.

PPP immunodepleted of coagulation factors FII or FVII or FIX or FX or both FII and FX was obtained from Haemotologic Technologies Inc. (Essex Junction, Vt., USA). The depleted plasma was mixed into pooled normal plasma in different proportions as described with each experiment below. Thromboplastin and calcium was added and clotting times were measured in progressively increasing dilutions of normal plasma with Owren's buffer.

ROTEM Experiments

Dynamic blood clot formation profiles were recorded by a ROTEM Thromboelastometry Coagulation Analyzer (Pentapharm, Munich, Germany) as described in detail elsewhere [Sorensen, B., et al., *J Thromb Haemost*, 2003. 1(3): p. 551-8. Ingerslev, J., et al. *Haemophilia*, 2003. 9(4): p. 348-52. Fenger-Eriksen, C., et al. *Br J Anaesth*, 2005. 94(3): p. 324-9] but differs in that instead of whole blood, citrated PPP was used. In brief, the reaction mixture contained 270 μl of citrated plasma+30 μl of buffer+20 μl dilute TF and $CaCl_2$. All results shown are means of four experiments. The thromboelastometry measurement (ROTEM) was based on activation of coagulation with highly diluted thromboplastin (final reaction mixture dilution of TF 1:17,000). Assessment of plasma clot formation was based on standard thromboelastometry parameters such as the clotting time (CT), maximum velocity (MaxVel) and the maximum clot firmness (MCF). The CT characterizes the initiation phase of clot formation. The MaxVel represents the propagation phase of clotting and the MCF indicates the stabilization phase.

ROTEM experiments were done on PNP dilutions made with the relevant factor deficient plasma (FII, FVII, FIX or FX) mixed in gradually with increasing proportion of normal plasma in order to make final coagulation factor concentrations of 1, 2, 4, 8, 16, 32 and 50%. The mixtures were diluted 1:600 in two steps with HEPES $CaCl_2$ buffer. The experiments were done without and with added platelet phospholipid or washed blood bank platelets. The experimental cuvettes were mounted in an aluminium cup holder that was thermostatically controlled at 37° C. Mixture of 270 μl of each plasma dilution and 30 μl of washed platelets were placed in the measuring cups. The measurement was started by adding 20 μl of the recombinatnt TF 1:600 dilution and placing the cup on a 6 mm diameter pin which is attached to the lower end of a vertical axis. Each experiment was done in quadruplicate.

Prothrombin Time

Both the Quick prothrombin time (PT) and the Owren's prothrombin time (prothrombin proconverting time, P&P test) were measured on patient samples. The STA-R coagulation analyzer was used (Diagnostika Stago, Asnieres, France). The PT was done using the STA-Néoplastine® CI plus as coagulation reagent, with and ISI value of 1.3 and the P&P was done using the STA-SPA 50 reagent with ISI of 1.01 (both from Diagnostika Stago). The P&P reagent is similar to the PT reagent but also consists of added absorbed bovine plasma as a source of coagulation factor V and fibrinogen and, thus, is only sensitive to the activity of FII, FVII and FX. The P&P percentages were calculated from a standard curve based on serially diluted pooled plasma in Owren's buffer. The INR is calculate as described above.

Statistical Analysis

The GraphPad Prism 5.0 statistical software (GraphPad Inc. CA, USA) was used for graphing and statistical calculations including linear and non-linear regression analysis. All data are shown as mean±1 standard error of the mean (SEM).

Results

Example 1

PT and P&P in Relation to Selective Reduction in Individual VKD Factors

Figure 1A:
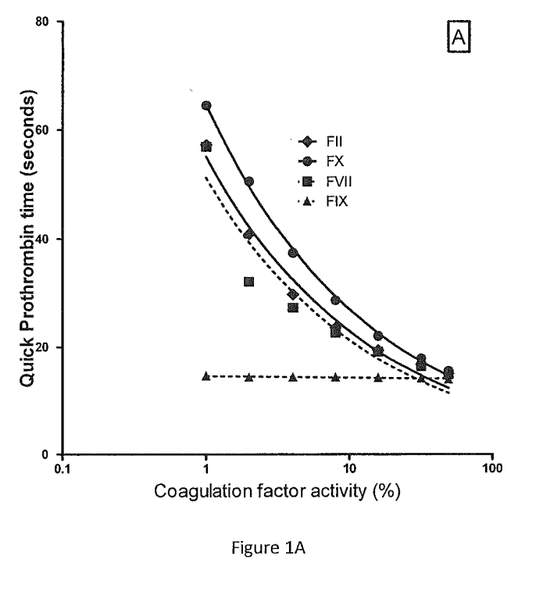
Figure 1B:
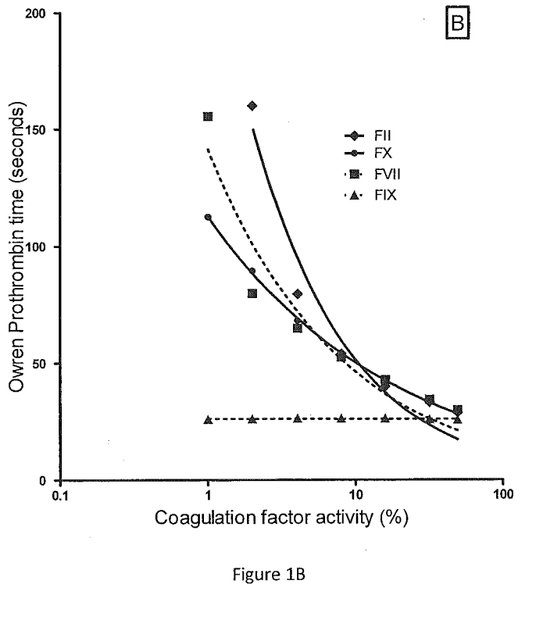

The relationship between PT and reduced concentration of selected VKD coagulation factors FII, FVII, FIX or FX in PPP is shown in FIG. 1. The Quick prothrombin time is shown in panel A and Owren's prothrombin time (P&P) in panel B. The experiments were done by gradually repleting plasma completely immunodepleted of a single factor by gradually mixing in normal plasma. As expected, both types of PT measurements (Quick and Owren) were equally sensitive to the concentration of FII, FVII and FX throughout the tested concentrations whereas neither measurement was sensitive to the FIX activity.

Example 2

Figure 2:
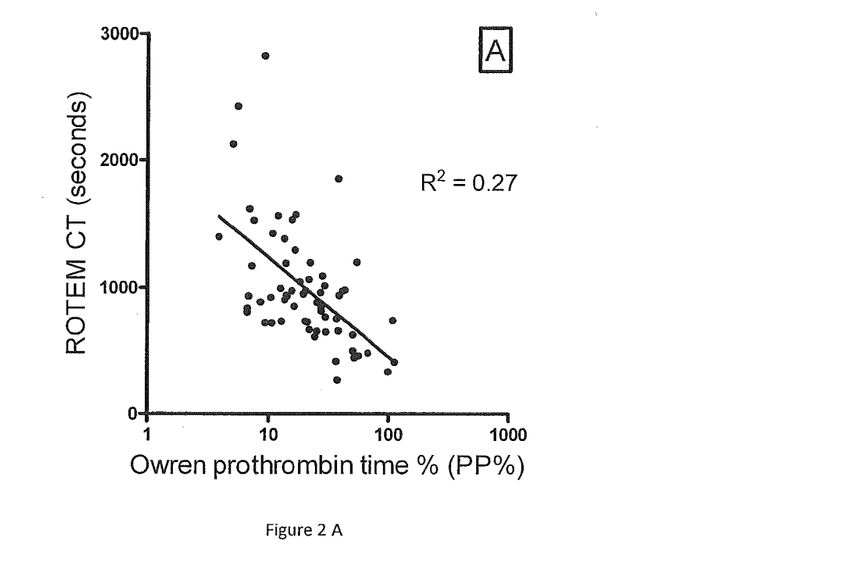
FIG. 2: ROTEM parameters in relation to P&P percentage in 65 samples from patients on stable anticoagulation with warfarin.

Correlation of ROTEM Parameters to Owren's PT in Samples from Patients on Warfarin ROTEM parameters and P&P test results were compared in PPP samples obtained from 65 consecutive patients on warfarin attending the anticoagulation clinic (FIG. 2). There was only a moderate correlation between the P&P test percent coagulant activity and the ROTEM CT ($R^2$=0.27, p<0.0001) with a marked variation in ROTEM CT at a similar P&P percentage. There was poor correlation between the P&P and the ROTEM Max Vel ($R^2$=0.08, p<0.0001) and the ROTEM MCF ($R^2$=0.11, p=0.0014). Similar results are seen if the INR is plotted against the ROTEM parameters (not shown). ROTEM parameters were also measured in adsorbed PPP equally depleted of all VKD factors. By mixing in progressively increased concentrations of pooled normal PPP, the adsorbed plasma was gradually repleted with equal concentrations of VKD factors. With all VKD factor concentrations equally reduced, a good correlation was found, i.e. $R^2$ by non-linear regression was 0.79 for the ROTEM CT, 0.64 for the ROTEM MaxVel and 0.77 for the ROTEM MCF (curves not shown).

Example 3

ROTEM Parameters in Relation to Selective Reduction of Individual VKD Factors

Figure 3A:
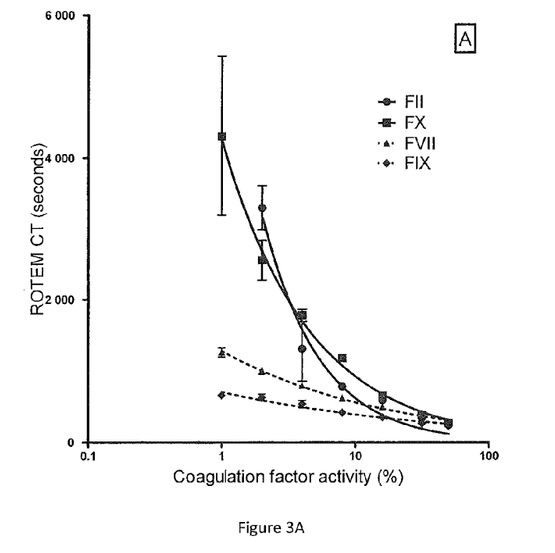
FIG. 3: ROTEM parameters (CT, MaxVel, MCF) in relation to selective reduction in individual vitamin K dependent coagulation factor activity in platelet poor plasma.
Figure 3B:
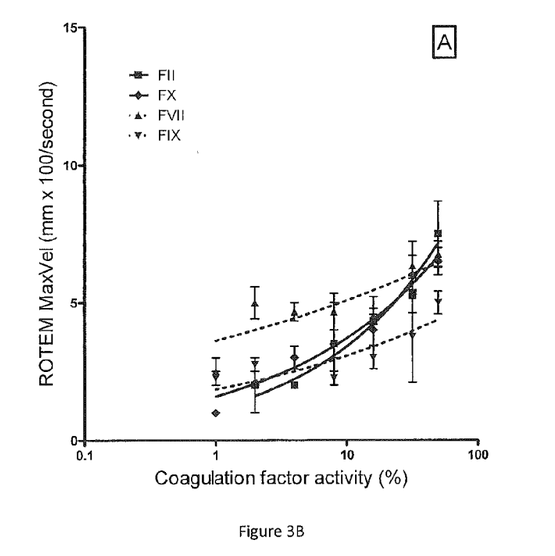
Figure 3C:
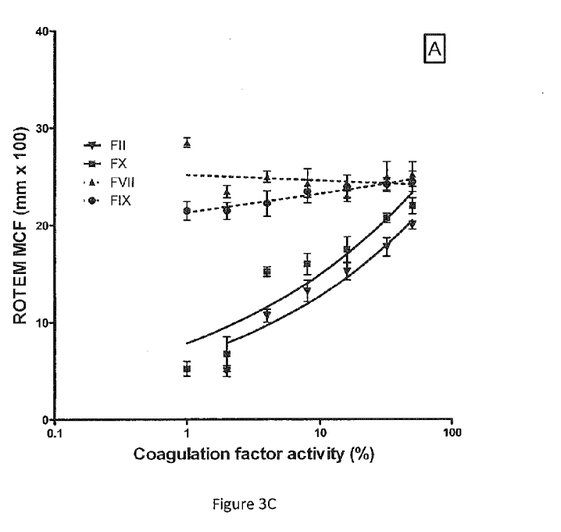

In order to separately evaluate the influence of each VKD factor on ROTEM parameters, we tested coagulation with ROTEM in PPP selectively immunodepleted of a single individual VKD factor and then gradually repleted the relevant deficient factor by mixing in normal plasma. The data shown in FIG. 3 relate to experiments in PPP without added platelet phoshpolipid or washed platelets. The ROTEM CT (initiation phase) (FIG. 3A) was prolonged markedly more by gradual selective reduction in FII or FX at mildly and moderately low levels (similar to those aimed for during anticoagulation) than by similar reductions in FVII or FIX. The results were similar in PPP with added platelet phospholipid and in PPP with added washed platelets (data not shown). The ROTEM Max-Vel (FIG. 3B) representing the propagation phase of ROTEM clot formation was also more dependent on the FII and FX concentration than on the FVII or FIX concentration in PPP and also in PPP enriched with platelet phospholipids (data not shown) but possible more dependent on II than X concentration with added washed platelets (data not shown). Finally, the stabilization phase or ROTEM MCF in PPP (FIG. 3C) was more dependent on FII and FX than on FIX or FVII.

Based on these ROTEM experiments, we conclude that FII or FX carry more weight on fibrin formation than do factors FVII and FIX at mildly and moderately reduced factor concentrations, similar to those present and aimed for during coumarin therapy. FII and FX had more influence on all phases of clot formation (initiation, propagation and stabilization) than FVII and FIX. The poor correlation of ROTEM parameters with the Owren PT (INR) described above in patient plasma samples possibly reflects this discrepancy between FVII on one hand and FII and FX on the other hand on clot formation in PT and ROTEM assays.

We also conclude that the combined effect of FII and FX may have considerably more weight on clot formation than do FVII or FIX at factor concentrations relevant to anticoagulant therapy. However, since FVII has much shorter half-life than FII and FX, fluctuations in prothrombin times (PT or P&P) may sometimes be mainly related to FVII concentration change and may not predict a true change in clot formation potential or in the antithrombotic effect. The confounding effect of FVII causing PT fluctuation could potentially lead to erroneous dosing of VKA and to unnecessarily frequent monitoring tests. Thus, the inclusion of FVII sensitivity in current monitoring tests may possibly reduce the efficacy and safety and increase the cost of coumarin therapy. It is contemplated that fluctuation in the anticoagulant effect of VKA could be reduced by eliminating the influence of FVII on monitoring tests.

Example 4

Fiix Method Applied on Sample Plasma

Fiix Method Based Test

Our invention is based on the idea that by mixing a plasma sample to be tested with plasma that is deficient (totally depleted) in factors FII and FX (herein referred to as Fiix-deficient plasma), thereby correcting for all other possible coagulation factor deficiencies in the sample, and subsequently measuring clotting time following activation of coagulation with a coagulation reagent, the test results will only reflect the activity of coagulation FII and FX.

The test results may be obtained as clotting time, clotting time ratio or any other endpoint measuring thrombin generation or fibrin formation. The experimental results demonstrated in the examples herein are based on measuring clotting times with thromboplastin (STA®—Neoplastine® CI plus from Diagnostica Stago) as the coagulation reagent on the STA-R instrument (Diagnostica Stago). Since this is a variant of the prothrombin time we call it "Fiix-prothrombin time" or Fiix-PT.

In our new method, which we call Fiix-method, a test plasma sample (patient plasma) is mixed with normal plasma that has been immunodepleted of both FII and FX (Fiix-deficient plasma). Using such mixture, by adding thromboplastin and calcium, a prothrombin time variant can be measured that is only sensitive to FII and FX, ie Fiix-PT. In the Fiix-PT the proportions of test plasma to Fiix-deficient plasma can be in the range from 1:1 to 1:20 parts, preferably in the range from 1:2 to 1:10 (see below).

Figure 4:
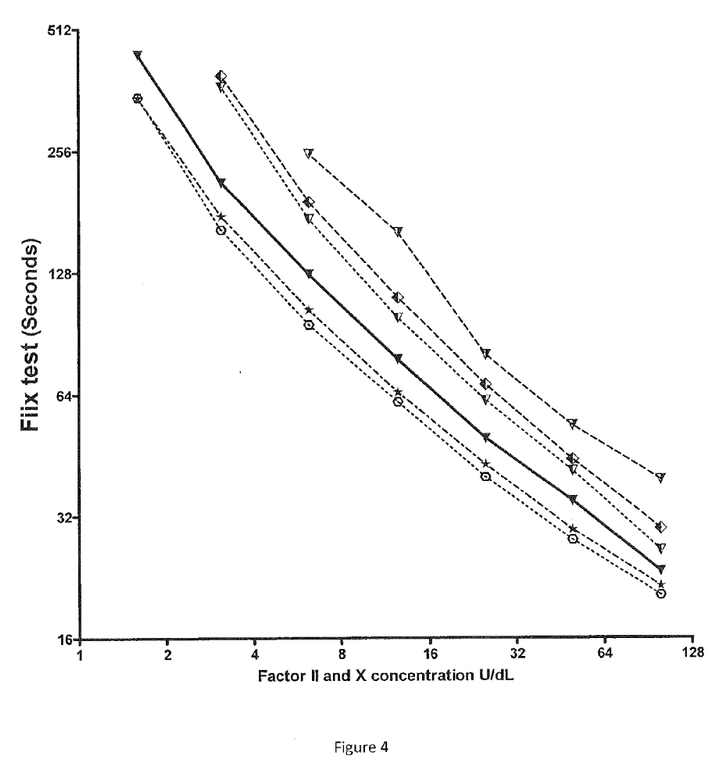
FIG. 4: Fiix-prothrombin time development; clotting times obtained on test plasmas with combined FII and FX activity ranging from 1.6% to 100%. The curves describe results with obtained with different experimental conditions, ie different proportion of test plasma to Fiix deficient plasma as well as different test plasma pre-dilution. Representative experiments show proportion of test plasma to total plasma (volume of test plasma+volume of Fiix plasma): -▼- 0.09 (1+10); -▼- 0.17 (1+5); -◆- 0.25 (1+3); -●- 0.28 (1+2.5); -▼- 0.31 (1+2.2); -★- 0.40 (1+1.5).

The demonstrative results from our experiments using thromboplastin as coagulation reagent (i.e. Fiix-PT) are shown in FIG. 4. The results show the clotting times obtained in relation to the "Fiix-percentage", ie percentage concentration of FII and FX combined. The different curves represent different dilutions of normal plasma as well as different ratios of normal sample plasma to Fiix deficient plasma in the mixture.

The ratio of test plasma and Fiix deficient plasma in the samples shown in FIG. 4 is as follows: -▼- 0.09 (1+10); -▼- 0.17 (1+5); -◆- 0.25 (1+3); -●- 0.28 (1+2.5); -▼- 0.31 (1+2.2); -★- 0.40 (1+1.5).

Different ratios were used but our aim was to be able to reliably measure FII and FX concentrations <2 u/dL (u refers to plasma equivalent units). In order to accurately measure FII and FX concentrations as low as <2 u/dL, the experimental results suggest that a preferable ratio of test plasma to Fiix-deficient plasma is in the range of 1:2-1:10.

Figure 5:
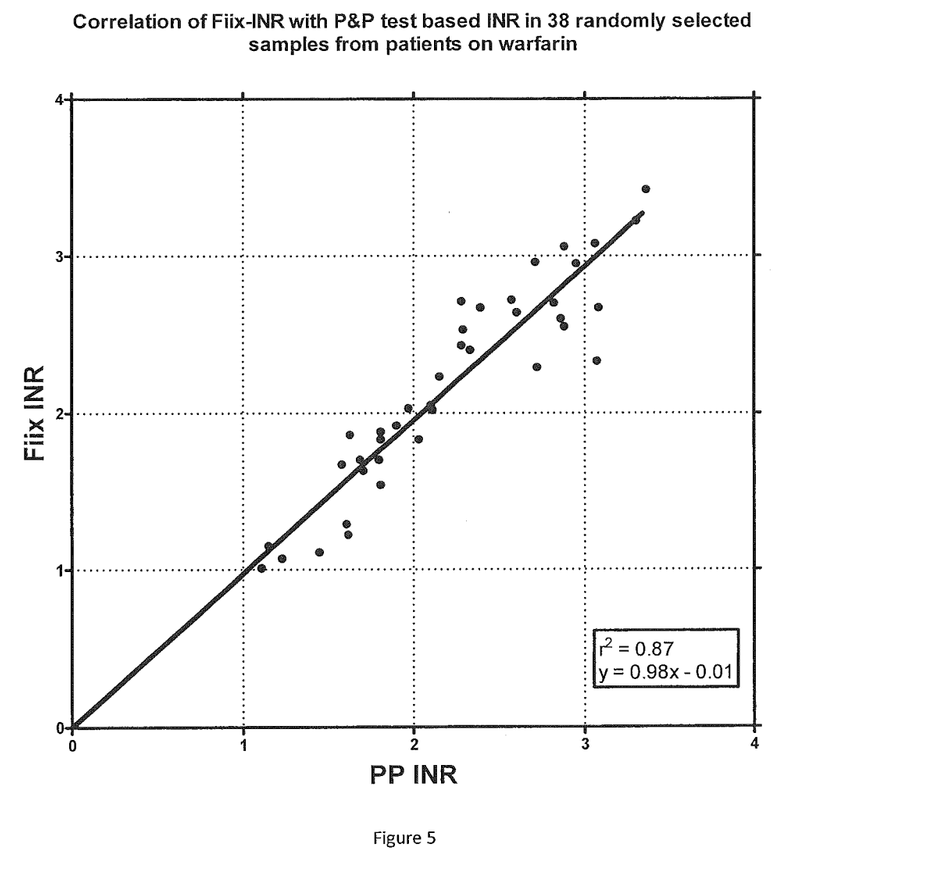
FIG. 5. Correlation of Fiix-INR with INR(PP-INR) in 38 randomly selected samples from stable patients on warfarin.

Based on the experiments shown in FIG. 4 we decided to measure the Fiix-PT by mixing 80 uL of a 1:7 dilution of test plasma with 25 uL of Fiix-deficient plasma (i.e. final proportion 1 part test plasma to 2.2 parts Fiix-deficient plasma). We then measured "Fiix-PT" in samples from 38 patients on stable warfarin therapy and calculated the international normalized ratio ("Fiix-INR"). As shown in FIG. 5, the Fiix-INR correlates well with the Owren's PT based INR values (PP-INR; $R^2=0.87$, $p<0.0001$). Corresponding results were found when Fiix-INR was correlated with Quick PT based INR (PT-INR, data not shown).

Figure 6:
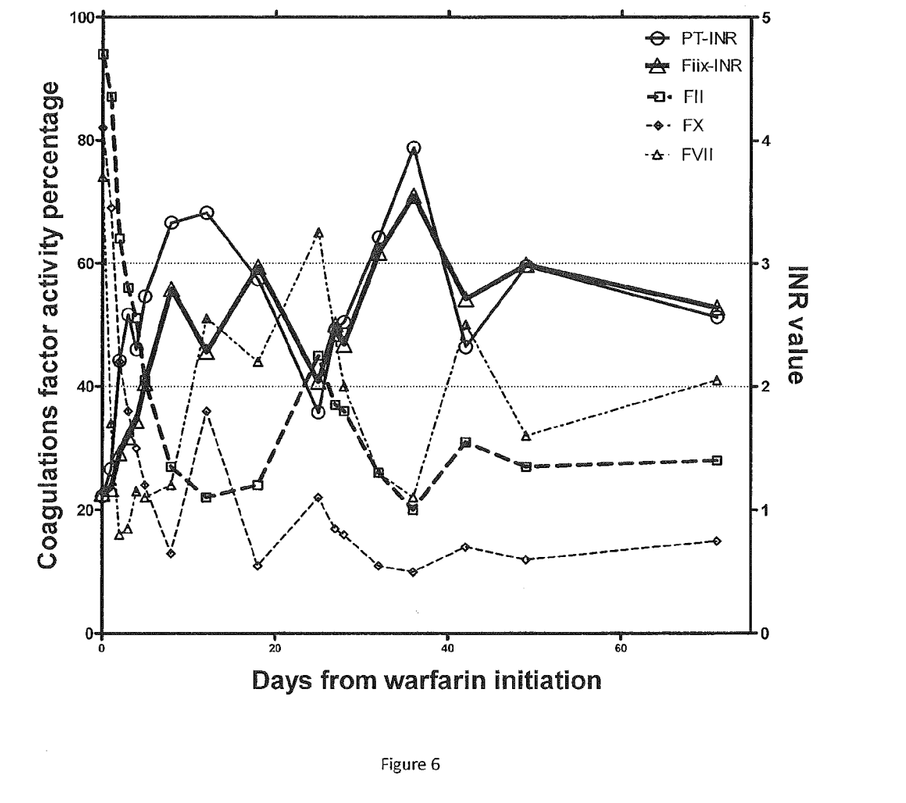
FIG. 6. Sequential measurements of FII, FVII and FX in a single individual beginning on warfarin in relation to INR (PP-INR, black curve) and Fiix-INR (red curve). The clotting times (INR) change in relation to changes in concentrations of the VKD factors.

In FIG. 6 we show sequential measurements of Fiix-INR, PP-INR, FII, FVII and FX over 49 days in a single patient starting on warfarin. The amount of coagulation factors (percentage) is shown on the left Y-axis and the INR value on the right Y-axis. The change in INR in relation to changes in concentrations of the VKD factors can be derived from the graph. In short, the PT-INR shows more fluctuation than the Fiix-INR, the reason being that the PT-INR responds to the rapid changes that occur in FVII but the Fiix-INR does not. However, since—based on the experiments previously discussed and our hypothesis based thereon, that the FII and FX concentration is mainly responsible for the antithrombotic effect of warfarin—we submit that the Fiix-INR more accurately describes the antithrombotic effect present in the patient.

In particular, it can be seen that the PT-INR value rises much quicker than the Fiix-INR the very first days of administration, this can be attributed to the fast reduction of FVII, which has an effect on the measured PT-INR value but not on the Fiix-INR value. The PT-INR value indicates that already on day 3, the patient has reached an acceptable anticoagulated range (grey zone) and the dip after day 4 indicates that the warfarin dose has likely been reduced. The Fiix curve, on the other hand, indicated that the patient reaches an acceptable INR value (acceptable anticoagulation) on day 5. The Fiix value remains in the suitable INR zone in the following days 6 and 7, whereas the PT-INR values erroneously indicate that the patient is receiving too high warfarin dose.

The invention claimed is:
1. A method for measuring the effect of a coumarin anticoagulant drug on coagulability in a patient taking said cou- marin drug, for the purpose of adjusting a dosage of said drug, which is based on measuring in a test plasma sample from said patient the influence of said anticoagulant drug on the combined activity of only coagulation factors II and X, the method comprising:

provided said test blood sample from said patient who has been administered the coumarin anticoagulant drug, mixing said test plasma sample with plasma that has been made deficient in only factor II and factor X, to provide a corrected plasma sample, which is normal-adjusted in all coagulation factors other than factor II and factor X, wherein the ratio of said test plasma sample and said plasma deficient in only factor II and factor X is in the range from 1:1 to 1:20, adding to said corrected plasma sample one or more coagulation reagents and calcium, determining blood clotting ability of said corrected plasma sample by measuring blood clotting time or thrombin generation, and adjusting the dose of said coumarin anticoagulant drug, to reach recommended a therapeutic INR of about 2 to about 3, such that the dose is increased to maximize the antithrombotic effect of the coumarin drug or the dose is decreased to minimize risk of abnormal bleeding caused by over-anticoagulation.

2. The method of claim 1, wherein said one or more coagulation reagent is selected from the group consisting of:
   i) thromboplastin,
   ii) phospholipids,
   iii) factor IXa,
   iv) factor XIa,
   v) factor XIIa,
   vi) kallikrein,
   vii) exogenous activator, including snake venoms that activate factor X, and
   viii) factor VIIa.

3. The method of claim 2, comprising adding a contact activator selected from the group consisting of
   i) kaolin particles,
   ii) celite,
   iii) glass particles,
   iv) silica particles, and
   v) ellagic acid.

4. The method of any claim 1, further comprising the step of diluting said test plasma sample with buffer or saline solution.

5. The method of claim 1, wherein said coagulation reagent is diluted with water, a saline aqueous solution or buffered aqueous solution.

6. The method of claim 1, wherein at least one component of said coagulation reagent, plasma deficient in only factor II and factor X, or calcium source is lyophilised, and wherein the method further comprises a step of reconstituting said at least one component.

7. The method of claim 1, wherein the step of determining blood clotting ability comprises a method selected from the group consisting of:
   manual/visual coagulation detection,
   mechanical and/or electronic methods for observing viscosity changes,
   optical methods of detecting clot formation,
   chromogenic detection using chromogenic substrates,
   fluorogenic detection using fluorogenic substrates, and
   luminogenic detection.

8. A test kit for measuring the activity of an anticoagulant drug in a patient, comprising:
   a coagulation reagent, and
   normal plasma that is deficient in only factor II and factor X and which contains factors including factor VII and IX.

9. The test kit according to claim 8 comprising in one container said coagulation reagent and said normal plasma that is deficient in only factor II and factor X and which contains factors including factor VII and IX.

10. The test kit of claim 8 comprising a source of calcium ions.

11. The test kit according to claim 8 comprising a first container comprising said coagulation reagent and said normal plasma that is deficient in only factor II and factor X and which contains factors including factor VII and IX.

12. The test kit of claim 8 comprising in a first container said coagulation reagent and in a second container said normal plasma that is deficient in only factor II and factor X and which contains factors including factor VII and IX.

13. The test kit according to claim 8, wherein said coagulation reagent is selected from one or more of
   i) thromboplastin,
   ii) phospholipids,
   iii) factor IXa,
   iv) factor XIa,
   v) factor XIIa,
   vi) kallikrein,
   vii) exogenous activator, including snake venoms that active factor X, and
   viii) factor VIIa.

14. The test kit according to claim 13, wherein said coagulation reagent comprises phospholipids, wherein the kit comprises in one container said coagulation reagent, a contact activator as described in claim 3, and said normal plasma that is deficient in only factor II and factor X and which contains factors including factor VII and IX.

15. The test kit according to claim 14, wherein said coagulation reagent and/or said normal plasma that is deficient in only factor II and factor X and which contains factors including factor VII and IX is lyophilized.

16. The method according to claim 1, wherein the artificially prepared plasma deficient in only factor II and factor X is produced by immunodepletion methods.

* * * * *